United States Patent
Regan

(10) Patent No.: US 6,872,075 B2
(45) Date of Patent: Mar. 29, 2005

(54) ENDODONTIC FILE WITH A METALLIC CONDUCTOR AS PART OF THE PLASTIC HANDLE TO FACILITATE USE OF ELECTRONIC APEX LOCATORS

(76) Inventor: John Edward Regan, 650 Cherry St., Huntington, IN (US) 46750-2095

( * ) Notice: Subject to any disclaimer, the term of this patent is extended or adjusted under 35 U.S.C. 154(b) by 135 days.

(21) Appl. No.: 10/101,822

(22) Filed: Mar. 21, 2002

(65) Prior Publication Data

US 2003/0180685 A1 Sep. 25, 2003

(51) Int. Cl.[7] ............................................. A61C 5/02
(52) U.S. Cl. ........................... 433/102; 433/27; 433/72
(58) Field of Search ............................ 433/27, 72, 32, 433/102; 600/589, 590

(56) References Cited

U.S. PATENT DOCUMENTS

| | | | | | |
|---|---|---|---|---|---|
| 3,753,434 A | * | 8/1973 | Pike et al. | ...................... | 433/32 |
| 3,916,529 A | * | 11/1975 | Mousseau | .................... | 600/547 |
| 4,243,388 A | * | 1/1981 | Arai | ............................. | 433/27 |
| 4,353,693 A | * | 10/1982 | Dery et al. | .................... | 433/27 |
| 5,112,224 A | * | 5/1992 | Shirota | ......................... | 433/27 |
| 5,421,727 A | * | 6/1995 | Stevens et al. | ............. | 433/224 |
| 5,775,902 A | * | 7/1998 | Matsutani et al. | .......... | 433/102 |
| 6,520,773 B1 | * | 2/2003 | Weber | .......................... | 433/27 |

* cited by examiner

Primary Examiner—Ralph A. Lewis

(57) ABSTRACT

This invention modifies hand root canal files used in dentistry by placing metallic contact areas on the plastic handle. This change makes using electronic apex locators to determine the length of the root canal much faster and easier.

3 Claims, 4 Drawing Sheets

ENDODONTIC FILE WITH A METALLIC CONDUCTOR AS PART OF THE PLASTIC HANDLE TO FACILITATE USE OF ELECTRONIC APEX LOCATORS

CROSS-REFERENCE TO RELATED APPLICATIONS

Not applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not applicable

BACKGROUND OF THE INVENTION

A. Field of Endeavor

This invention applies to the field of dentistry and, more specifically, to endodontics within that field.

B. Description of Prior Art

At the current time (Feb.-15-2002), endodontic files and reamers with metal shafts and plastic handles are commonly used to clean and measure the length of root canals in teeth with the aid of electronic apex locating devices. This is accomplished by placing a file in the root canal and then attaching or touching a special probe or file holder from an electronic apex locator to the metal shaft of the file to complete an electronic circuit.

The problem commonly encountered by this system is one of access to the metal shaft in the posterior teeth where short files are needed most often but, frequently, end up with the shaft totally within the crown of the tooth being treated. When endodontics is performed on teeth with metal crowns, the metal shaft of the file or the metal probe will short circuit the apex locator if either touch the metal restoration. Insulating sheaths are available to cover the file shaft but they also limit access for the probe. On occasion, a cut is made through the plastic handle to reach the extension of the metal shaft in the handle in order to get an accessible contact point for the probe.

The above problems result in extended treatment time which translates into additional cost for this procedure.

Prior Art Pike et al (U.S. Pat. No. 3,753,434), Mousseau (U.S. Pat. No. 3,916,529), Arai (U.S. Pat. No. 4,243,388), Dery (4,353,693), Shirota (U.S. Pat. No. 5,112,224), Stevens (U.S. Pat. No. 5,421,727), Matsutani et al (5,775,902) and Weber (U.S. Pat. No. 6,520,773) are made of record.

BRIEF SUMMARY OF THE INVENTION

A. Statement of the Object of the Invention

All of the problems cited above could be circumvented if a metallic contact point or points could be developed in the plastic handle of the file which almost always extends past the crown of the tooth and is, therefore, readily accessible to the electronic apex locator probe.

B. Invention Summary

The essence of this invention is to modify the plastic handles on existing endodontic hand files and reamers so that a metallic contact point (or points) is available in this area.

The probes and file holders from electronic apex locators would have easy access to a contact point in the handle area. This design would also allow the use of insulating sheaths over the metal shafts to prevent short circuits when operating through metal restorations.

Figure 1:
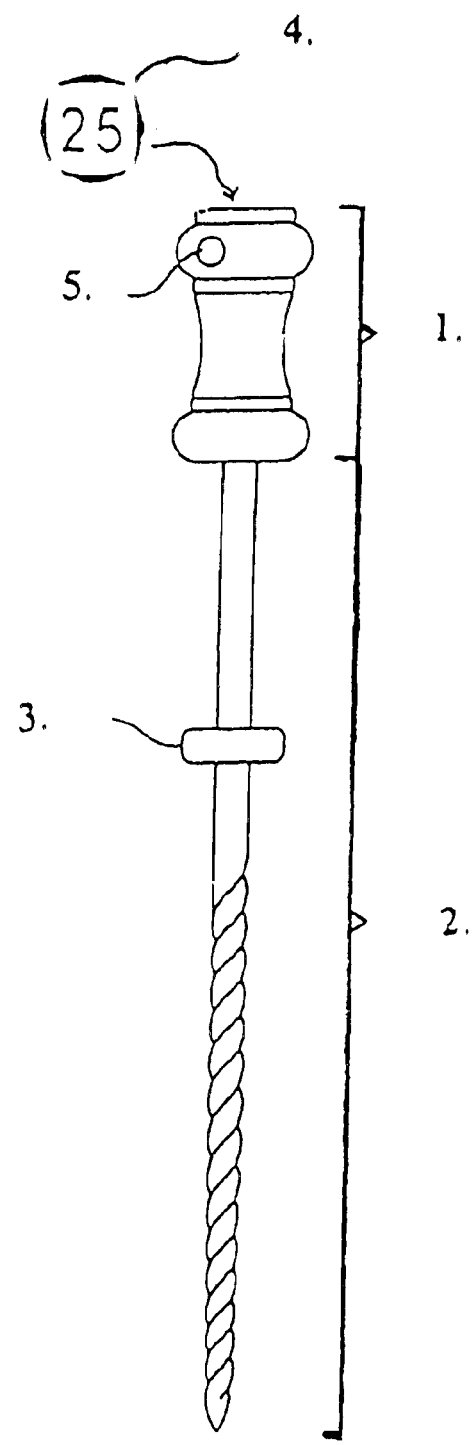
FIG. 1: Standard, Unmodified Endodontic Hand File or Reamer (Prior Art).

Not to scale. This drawing represents a standard type endodontic hand file or reamer with a typical plastic handle (1), metal shaft (2), adjustable rubber stop (3) and end marking (4) signifying the size of the file. It also shows a hole (5) at the proximal end of the plastic handle used to attach dental floss. Most manufacturers color code their files and size them to ISO specifications. These characteristics are not part of the invention. Modifications proposed for the plastic handle in subsequent drawings are the proposed invention. Files and reamers come in various sizes and shapes including the design of their plastic handles from various current manufacturers so scale and these characteristics are not a part of the invention.

Figure 2:
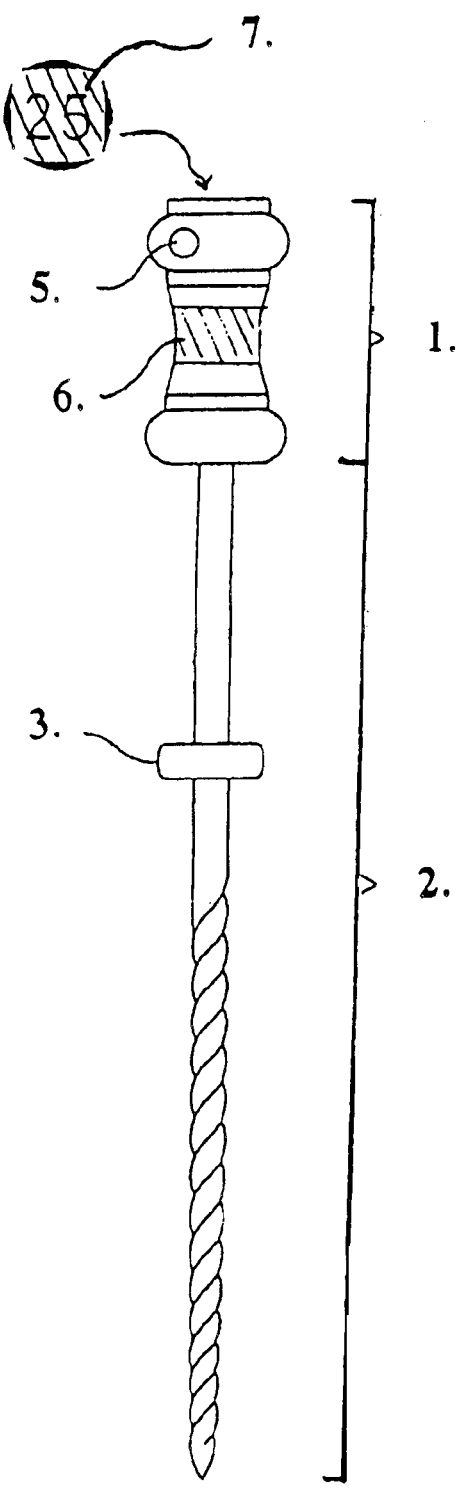

B. FIG. 2: Modified Endodontic Hand File or Reamer Showing Invention.

Not to scale. This drawing represents a standard type endodontic hand file with metal shaft (2) and plastic handle (I) as modified with a metallic ring (6) as part of the handle and a metallic end cap touch plate (7). The adjustable rubber stop (3) is also shown.

Figure 3:
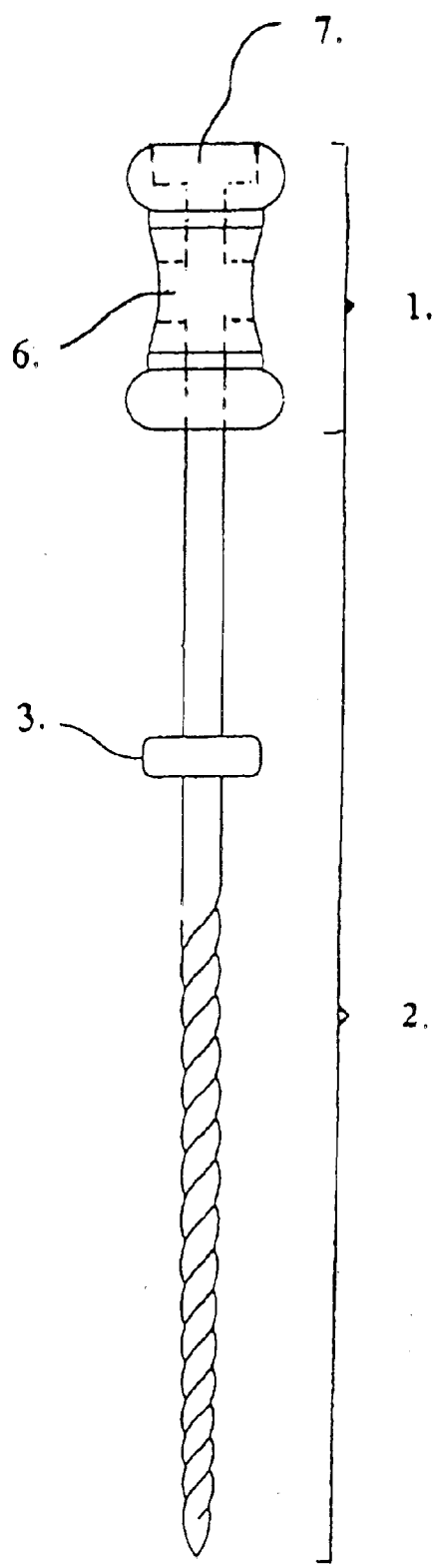

C. FIG. 3: Schematic Drawing of Internal Design of Handle Modification.

Not to scale. This drawing represents a schematic view of the inside of the plastic handle after it has been modified. The view shows the typical plastic handle (1) modified with a metallic ring (6) and a recessed metallic proximal touch plate (7) connected to the metal shaft (2). The adjustable rubber stop (3) is also shown.

Figure 4:
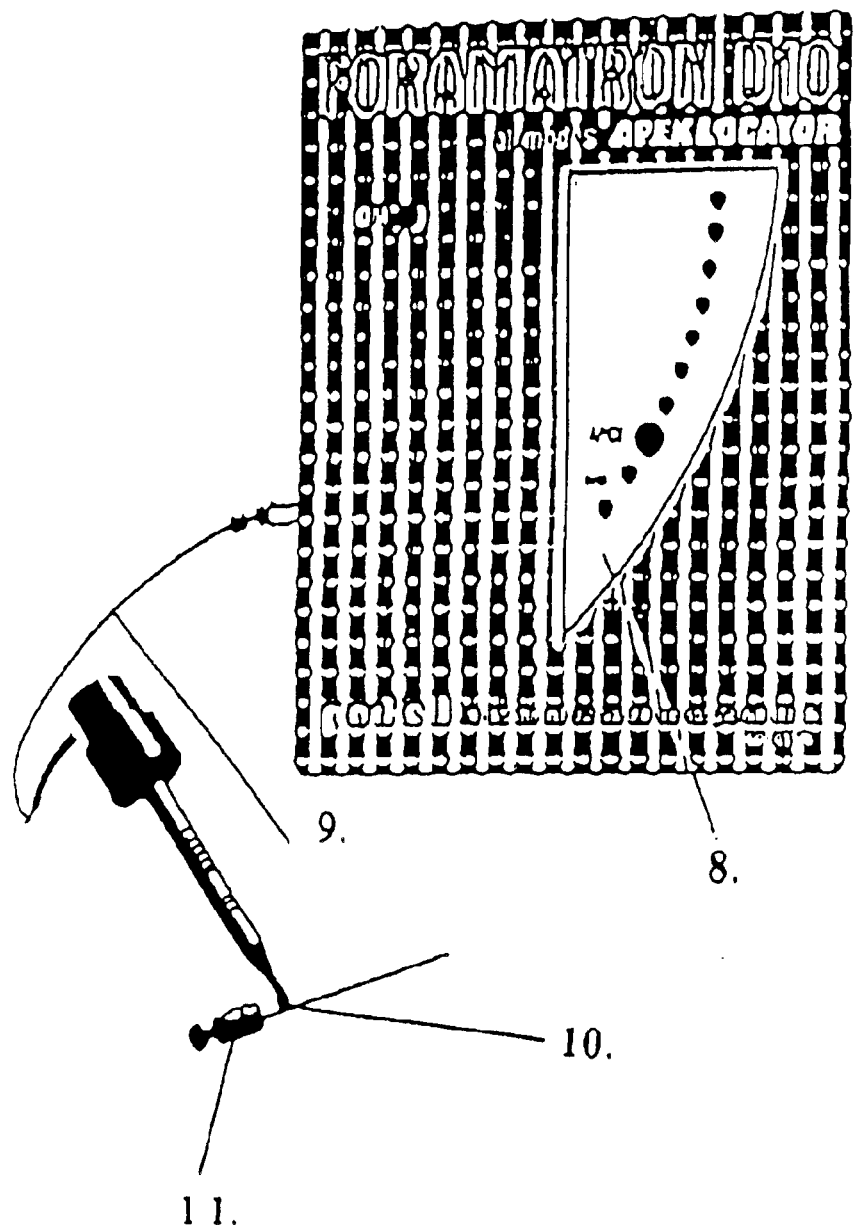

D. FIG. 4: A Representative Electronic Apex Locator and Clip (Prior Art).

Not to scale. This equipment is presented for reference only and is not part of the invention. Locators are presented because they are frequently referred to above and they are the reason why the invention modifications are important. In this view, an example of an electronic apex locator (8) is shown connected to the file clip (10) by a connecting wire (9). The clip (10) is attached to the metal shaft of a standard unmodified endodontic file or reamer (11).

DETAILED DESCRIPTION OF THE INVENTION

1. General Description

This invention is a modification of a standard endodontic file or reamer (FIG. 1). The modification consists of (FIG. 2) placing a metallic contact area in the plastic handle (6 and 7) of the file or reamer as described above and below.

2. The Old Technology

Current hand endodontic files and reamers (FIG. 1) with plastic handles do not have a metal contact point in the handle making it very difficult to utilize electronic apex locators in many circumstances. Note in FIG. 4 how the clip grips the file below the plastic handle on the metal shaft (10). Files frequently extend into the tooth up to the plastic handle making it difficult to attach the clip or probe.

3. Improvement Invented

The improvement invented consists of placing a metallic contact area in the plastic handle where none now exists. See FIGS. 2 and 3. The problems with the current state of the art and improvements proposed by this invention were stated above under BACKGROUND OF THE INVENTION.

FIG. 2 represents a standard type endodontic file which has had the plastic handle modified by placement of a metal ring as part of the handle (6) and by addition of a metallic end cap touch plate (7). Electronic conduction can now be obtained by touching the metallic plate at the end of the handle (square with size number 25 on it) or by touching or clamping the metallic ring in the handle (6). Its location in the handle is not the essence of the invention nor its diameter.

Likewise, the geometric design of the metallic end plate (7) is not the essence of the invention. It could be round as shown in FIG. 2, or any other design. The size number remains desirable stamped on the metallic end plate but is not part of the invention. Standard files usually have a hole through the handle near the end cap (5) for dental floss to pass through and this feature should and could be retained but, once again, this feature is not part of the invention.

FIG. 3 shows a schematic drawing of the internal design of the handle after it has been modified as part of the invention. It has significant differences from the standard design currently in use. First, it is imperative that the metallic ring (6) and metallic end plate (7) be connected to the metal shaft (2). This connection could be made in any number of ways or could even be one solid piece of metal. Electrical conduction must be continuous from the tip of the metal shaft in the root canal to the metallic plate in the handle for the electronic apex locator to work properly.

The invention may consist of only the metallic end plate (7), only a metal ring around the handle (6), only a metallic bar(s) or wire(s) or coating on the handle or any combination so long as a metallic connector is provided in the handle area for contact with the electronic apex locator probe or file holder (10) examples of which are shown in FIG. 4.

4. How to Use the Invention

The invention is used by simply touching or connecting a probe or file holder (10) from the commercially available electronic apex locators (FIG. 4) to the contact area in the plastic handle rather than to the metal shaft below the handle (10) which is often difficult to access.

5. How to Make the Invention

There are several file manufacturers in the world. A variety of final configurations of this invention are possible with each presenting its own manufacturing technique. The essence of the invention may be inculcated into existing product lines by different methods by different firms.

The essential elements of the metal shaft and plastic handle would not change. If a metal ring, bar or end plate are added they must be in contact with the metal shaft in order to get conduction from the apex of the tooth to the electronic device. These elements may be joined as a solid unit, cast, machined, stamped, soldered, welded or by any other method preferred by the manufacturer.

These instruments are used and discarded with such rapidity that they must be made in large quantities which requires a firm with such equipment and experience.

What is claimed is:

1. An endodontic file for use in root canals comprising:

an elongated metal shaft having proximal and distal ends, said distal end of said shaft being adapted to extend into a dental root canal to the root canal's apex, and an enlarged handle connected to and surrounding the metal shaft proximal end, said handle comprised of an insulating material forming a body having a circumference and an electrode metal ring that extends about a portion of the body circumference, said electrode metal ring being electrically connected to said elongated metal shaft through said plastic body, wherein electrical current may be conducted from the distal end of the shaft to the electrode metal ring.

2. The endodontic file of claim 1, wherein said insulating material of said handle is plastic.

3. The endodontic file of claim 1, further including a metallic plate recessed in the proximal end of said handle that is electrically connected to said elongated metal shaft through said handle body and is accessible for touch contact.

* * * * *